United States Patent [19]

Müller et al.

[11] 4,385,965

[45] May 31, 1983

[54] PROCESS FOR THE RECOVERY OF PURE METHYLAL FROM METHANOL-METHYLAL MIXTURES

[75] Inventors: Wolfgang H. E. Müller; Manfred Kaufhold, both of Marl, Fed. Rep. of Germany

[73] Assignee: Chemische Werke Huls A.G., Marl, Fed. Rep. of Germany

[21] Appl. No.: 342,975

[22] Filed: Jan. 26, 1982

[30] Foreign Application Priority Data

Nov. 28, 1981 [DE]   Fed. Rep. of Germany ....... 3147320

[51] Int. Cl.³ .............................................. B01D 3/26
[52] U.S. Cl. ........................................ 203/75; 203/78; 203/82; 203/84; 203/94; 203/98; 568/594; 568/913
[58] Field of Search .................. 568/594, 913; 203/73, 203/77, 78, 93, 94, 80, 81, 82, 84, 98, 75, 18

[56] References Cited

U.S. PATENT DOCUMENTS 1,850,836   3/1932   Guinot ............................... 568/594

OTHER PUBLICATIONS

Robinson and Gilliland, Elements of Fractional Distillation, 4th Edition, pp. 196–212.

*Primary Examiner*—Frank Sever
*Attorney, Agent, or Firm*—Millen & White

[57] ABSTRACT

In a process for recovering pure methylal from methanol-methylal mixtures, which can optionally contain still further compounds, the separation conducted in a rectification device comprising two rectifying columns. In the first rectifying column, the mixture to be separated is rectified under a pressure lower than that in the second column, into a methylal-rich, methanol-poor distillate, and into a practically methylal-free, methanol-rich sump product. The methylal-rich distillate of the first rectification is then separated in a second rectifying column, operated under a higher pressure than the first rectification column, into a compound stream containing methanol and methylal, which is then recycled to the first rectifying column, and into pure methylal as the sump product. In a specific refinement, the first rectification is preferably operated under a pressure of 1–22 bar absolute and the second rectification preferably under a pressure of 9–30 bar absolute, with the second rectification being operated under a pressure which is at least 8 bar higher than that of the first rectification.

24 Claims, 2 Drawing Figures

PROCESS FOR THE RECOVERY OF PURE METHYLAL FROM METHANOL-METHYLAL MIXTURES

BACKGROUND OF THE INVENTION

This invention relates to a process for the recovery of pure methylal from mixtures of methylal and methanol, which will often contain substances such as water, formaldehyde, methyl formate, as well as others. More specifically, the invention especially relates to a process for obtaining pure methylal from mixtures produced in the synthesis of methylal from a formalin solution and methanol.

It is known in the prior art to produce an approximately 8% strength methanol-containing methylal mixture in an industrial process employing iron (III) chloride as a catalyst, and requiring no specialized technical equipment (see Houben Weyl "Methoden der organ. Chemie" [Methods of Organic Chemistry], vol. VI/3, Oxygen Compounds 1, Part 3 [1965]: 207). In this type process iron (III) sulfate is preferably used in place of iron (III) chloride to avoid chlorinated toxic by-products in the production of the methylal mixture.

It is desirable to recover substantially pure methylal from these mixtures. However, this cannot be readily accomplished by means of a simple rectification because of the existence of an azeotrope. In order to reduce the methanol concentration below 8% various alternative physical or chemical processes have been recommended for the separation of these amounts of methanol.

One such method is taught in Volkov and Ivanov (Vysokomolekul. Soedin 8 (8): 1459–61 [1966]) and Vinokurov (Nauch. Doklady Vysskei Shkoly. Lesoinzhener. Delo. 1958 No. 4: 193–195) wherein the methylal is purified by chemically reacting the methanol present with metallic sodium. Another prior art process teaches that the methanol can also be removed by extraction with concentrated aqueous calcium chloride solution, and by subsequent drying of the methylal (Ullmanns Encyclopaedie der technischen Chemie [Ullmann's Encyclopedia of Technical Chemistry] 3rd ed, vol. 3: 15). Still other known prior art processes for the separation of methanol and methylal include extractive distillation with various extraction agents including among others, water (German Pat. No. 1,002,305 and U.S. Pat. No. 2,545,889), aqueous alkaline solutions (U.S. Pat. No. 2,990,340, Vinokurov, Gidroliz. i Lesokhim. Prom. 12, No. 5: 4–6 [1959]), ethylene glycol (German Pat. No. 1,127,339), paraformaldehyde (Vinokurov, Gidroliz. i Lesokhim. Prom. 12, No. 5: 4–6 [1959]), as well as dimethylformamide (German Pat. No. 1,172,677).

Still another prior art method teaches the chemical reaction of methanol with excess aldehyde to obtain the acetal, i.e., methylal, (Russian Pat. No. 121,443). Likewise, Vinokurov (Izvest. Vysshikh Ucheb. Zavedenii, Lesnoi Zhur. 2, No. 2: 155–159 [1959]) compares three different methods for the separation of methanol and methylal. More specifically, the methods compared are the reaction of methanol with paraformaldehyde, the treatment of the azeotropic mixture of methanol and methylal with sodium hydroxide, and the distillation, as well as rectification, in the presence of an excess of formalin solution.

All of these disclosed processes serve to obtain higher purities in methylal yield by reducing methanol concentration but suffer the disadvantage that all require the use of additional materials. As a result these processes are very expensive and, in part, obtain relatively poor yields of methylal because of the involvement of some of the methylal in the reactions.

It is furthermore known to break an azeotrope by conducting a two step distillation at two different pressures. However, these are systems which have such advantageous properties, that the rectification under different pressures is better than the other above-discussed processes for the separation of the components; these systems are very rare. So it is taught in "Elements of Fractional Distillation" 4th ed. Robinson and Gilliland at page 212, that in view of the high heat consumption and the large number of plates required, other methods are more economical. Moreover, it is an exceptional advantage of this invention to the prior art, that not only is the azeotrope separated, but also the by-products such as methyl formate are removed without additional expense.

SUMMARY OF THE INVENTION

Thus, it is an object of the invention to provide a method for separating impure methylal from other components such as methanol, thereby resulting in high quantitative yields of methylal, which method neither results in substantial losses of methanol, nor requires the use of foreign substances. Thus, the method provides that a high purity of the thus-obtained methylal can be attained without requiring extensive purification steps.

It is another object of the invention to provide a novel purification process for methylal which is, in addition, simple and economical.

Upon further study of the specification and appended claims, further objects and advantages of this invention will become apparent to those skilled in the art.

The invention comprises rectifying a crude product containing methylal, methanol, and in some cases still other compounds, in two rectifying columns operated under different pressure. The first column is operated under a lower pressure wherein an azeotropic mixture of methylal-methanol, still containing perhaps more readily boiling components such as methyl formate, is distilled off from the excess methanol therein, and any other higher-boiling compounds, such as water, for example, which remain in the sump.

The distillate, i.e., the azeotrope, from this first rectifying column is separated in a second rectifying column, operated under a higher pressure than the first column, into a methanol-containing stream of materials which includes relatively large proportions of methylal, e.g., 70 to 85% by weight, and pure methylal as the sump product. The methanol-containing compound stream is then withdrawn from the second column at the column head.

When a highly volatile component, e.g., methyl formate, is present in the feed it is preferred that the methanol-containing compound stream is withdrawn as a side stream from the enrichment section of the second column, and the more readily boiling compounds, such as methyl formate, which are present in the initial raw material stream, are withdrawn in a high concentration from the head of the second column.

As a result of the second rectification, a substantially pure methylal product free of methanol, as well as being substantially free of methyl formate and water, is obtained as the sump product of the second rectification column. The distillate containing methanol and methylal from the second rectification is then returned to the first rectification column wherein it is again separated along with the initial feed stream.

DETAILED DISCUSSION OF THE INVENTION

Figure 1:
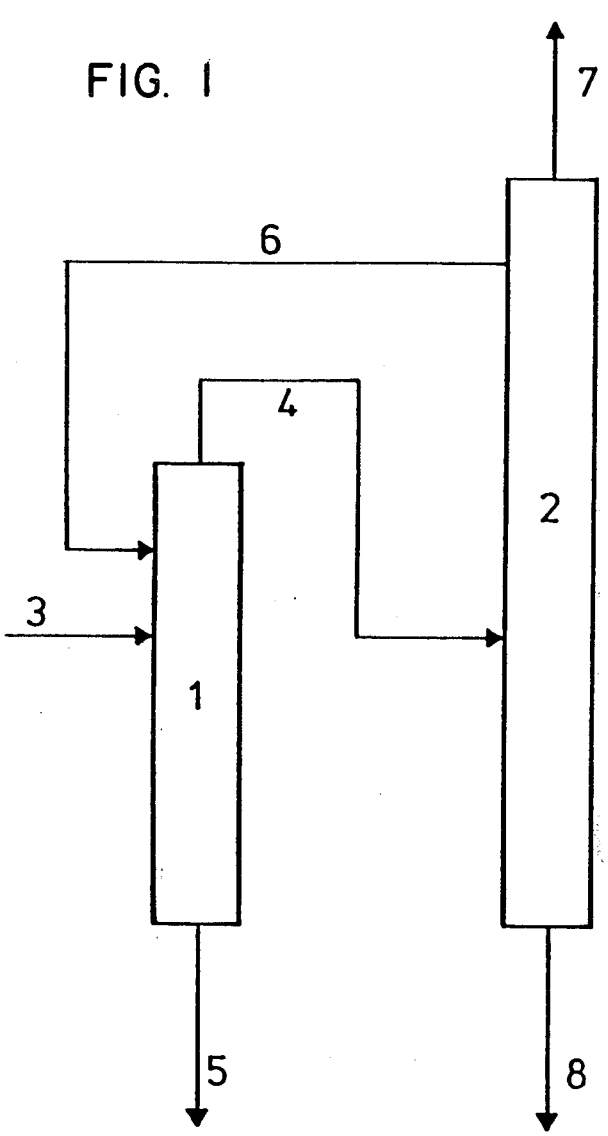
FIG. 1 is a schematic diagram of a first embodiment of an arrangement of columns for conducting the process according to the invention.

As discussed above, it is clear that the essential features of the process of this invention reside in that rectification is conducted in two rectifying columns, wherein the second rectification is conducted under a higher pressure than the first. More specifically, the first rectification is conducted under a pressure of 1–22 preferably 1 to 2 bar absolute, and the second rectification is effected under a pressure of 9–30 preferably 10 to 15 bar absolute, and the second rectification is carried out under a pressure which is higher than the pressure of the first rectification by at least 8, preferably at least 9 bar.

In the event that low-boiling compounds, such as methyl formate are present, a partial stream of the methylal-containing distillate from the second rectifying column can be discarded. However, this results in a reduction in the total yield of methylal, and it is preferable in another embodiment, to separate the distillate from the second column by further rectification, into a stream of almost pure low-boiling compounds which are removed from the process, and a mixture of methanol and methylal almost free of low-boiling compounds, which is reintroduced into the first rectifying column.

Conversely, this further rectification can be conducted in a third column arranged to receive a distillate containing methylal-methanol and low boiling compounds for separation therein.

It is therefore possible, to separate a mixture of methanol and methylal, which also comprises more readily boiling compounds such as methyl formate, in a system of three columns. The raw material is fed to the first column in which this feed and a recycled stream which is also fed to this column and consisting of methanol and methylal, is separated in a distillate consisting of methylal, some methanol and low-boiling substances as methyl formate and a sump product consisting of methanol. The distillate of the first column is separated in the second column, which is operated under a higher pressure than column 1, in a distillate consisting of methanol, low-boiling substances as methyl formate and methylal and a sump product consisting of very pure methylal. The distillate of the second column is separated in a third column in a distillate, which is rich on low-boiling substances e.g. methyl formate and a sump product, which is poor in low-boiling substances as methyl formate. This is recycled to the first column.

It is also possible to separate such a mixture which contents water. In this case the sump product of the first column contains all the water together with the methanol of the feed stream.

This embodiment wherein the low-boiling compounds are separated in a further rectification is particularly advantageous, and in this version, a methanol- and methylal-containing side stream, depleted of low-boiling compounds, 15 to 30% by weight methanol, 0 to 3% by weight methyl formate and 67 and 85% by weight methylal, is withdrawn from the enrichment section of the rectifying stage and recycled to the first stage, and a distillate depleted in methanol and methylal is removed from the head of the stage, while pure methylal is recovered in the sump thereof.

In all embodiments, the sump product from the first rectification, consisting essentially of methanol and water, can be separated into its components in a conventional process, for example, by a conventional rectification process. Furthermore, it should also be noted that the process of this invention is preferably conducted continuously.

A significant advantage of the process of this invention resides, as compared to the prior art, in that it comprises a particularly simple technique which can be readily automated, since only simple rectification stages are utilized without requiring introduction of foreign materials such as is done in conventional extractive and aezeotropic distillation techniques. Furthermore, the process does not result in significant methanol losses, and produces fairly high quantitative yields of methylal.

The process of the invention is flexible, since it makes possible the processing in a single plant of raw materials of varying compositions, e.g., methylal and methanol, including or not including other substances, such as, e.g., methyl formate. In addition, the process is economical and can optionally also be utilized in separating very large quantities of materials. Finally, the process is harmless to the environment because no additional materials are required which can lead to environmental pollution or contamination of the product.

The following table sets forth the weight percent analysis of feedstream which are particularly amenable to separation by the present invention:

| Component | General Range* | Preferred Range* |
|---|---|---|
| Methylal | 95 to 1% by weight | 94 to 40% by weight |
| Methanol | 5 to 99% by weight | 6 to 60% by weight |
| Methyl formate | 0 to 10% by weight | 0 to 3% by weight |
| Water | desired | desired |

*anhydrons calculated

The mixture of methanol and methylal recycled from the second rectification to the first rectification, preferably contains 15 to 25 weight percent methanol and preferably contains 85 to 75, especially to 80 percent methylal and in case small amounts of methyl formate. The weight ratio of the recycle stream to the azeotropic mixture passed to the second column is preferably about 0.15:1 to 0.6:1, especially about 0.2:1 to 0.4:1. The preferred reflux ratio of the first column is about 0.8 to 3.0 in the second column about 0.65 to 1.2 with regard to the recycled stream to the column 1, in relation of the concentration of methyl formate also essential higher reflux ratios on the top of the column; and if a third column is used, about 40 to 400. The more preferred reflux ratios of the first, second and, if used, third columns are respectively 1 to 2; 0.8 to 1 and 45 to 100.

The substantially pure methylal recovered by this invention analyzed by weight ist preferably at least 99.9% methylal with preferably less than 0.01% methanol, preferably less than 0.01% water, and less than 0.001% methyl formate.

Furthermore, although the pressure of the second column is at least 8 bar above that of the first, it is preferred that the pressure be 9 to 15 bar above, and more preferably 10 to 12 bar above that of the first stage. The operational pressure of the first stage is 1–22 bar absolute, preferably 1 to 3 bar, and more preferably 1 to 2 bar, with the pressure of the second stage at 9–30 bar absolute, preferably 10 to 18 bar, and more preferably 10 to 15 bar.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 50 parts by weight of methanol and 50 parts by weight of methylal was fed continuously in the liquid phase at the boiling temperature to the 15th practical plate (counted from the bottom) of the first rectifying column containing 35 practical plates in total. At the 16th plate, counted from the bottom, the head product from a second distillation column was also introduced, in the liquid phase, at the boiling temperature into the first rectifying column. The first rectifying column was operated under atmospheric pressure. At the head of the first column, with a reflux ratio of 2, a product was obtained analyzed to be 95.0% by weight methylal, and the sump of the column yielded a methanol product with about 10 ppm by weight of methylal. The product with 95% by weight of methylal obtained at the head was conducted into the middle, between the head and the sump of the second column, it being a packed column containing 35 theoretical plates. The second column was operated under a pressure of 10 bar absolute at the column head. In this column, operating at a reflux ratio of 0.9, a distillate with 15.9% by weight of methanol, remainder methylal, was withdrawn from the head of the column and recycled to the sixteenth plate of the first column. Pure methylal was obtained at the column sump of this second rectifying stage, containing only 10 ppm by weight of methanol.

EXAMPLE 2

This test was conducted as described in Example 1. However, the second column used had a height greater than the first column by 50%, with the feed into the second column effected at a point ⅓ the height of the second column, and a liquid side stream was withdrawn at ⅔ the height of the second column. No distillate was discharged at the head of the column as a result of no low-boiling compounds such as those in Example 1 being present in the raw material feed, i.e., the feed comprising a 50% methylal/50% methanol feed. The amount of the side stream, withdrawn in the liquid phase at a location ⅔ from the bottom of the second column, which was recycled into the first rectifying column corresponded to 52.6% of the amount of liquid flowing at this location through the column. The same results were obtained as in the case of Example 1.

EXAMPLE 3

The test was carried out in a manner similar to that in Example 2, except that the feed to the first column in this case contained 50 parts by weight of methylal, 49 parts by weight of methanol, and 1 part by weight of methyl formate. With a reflux ratio of 2, the distillate, amounting on a weight basis of 76% on the aforementioned feed, was removed from the head of the first column and conducted to the second column. From the second column, a side stream of 25% by weight, based on the feed to the first column, was removed and recycled to the first column. At the sump of the first column, a methanol product was obtained, amounting to 49% by weight of the feed, and containing only 0.1% of methylal, and free of methyl formate. From the head of the second column, operated under a pressure of 10 bar, about 1% based on the feed to the first column was withdrawn at a reflux ratio of 50. As a side stream 25%, based on the feed to the first column, was returned to the first column. About 50% of methylal, based on the feed to the first column, was obtained in the sump of the second column, with less than 10 ppm by weight of methanol and devoid of methyl formate.

EXAMPLE 4

The test was conducted in a manner similar to that of Example 3. However, a raw material feed containing 20% by weight of water, 40% by weight of methylal, 39.2% by weight of methanol, and 0.8% by weight of methyl formate was employed. About 66% by weight based on the feed, of distillate with a reflux ratio of 3 was removed from the first column, introduced to the second column, and with a recycling of the side stream of 25%, based on the feed to the first column, from the second column into the first column, a sump product was obtained in the first column amounting to 59%, based on the feed, with a composition of about 33.9% water, 66.0% methanol, and 0.1% methylal.

The mode of operation and the concentrations in column 2 were the same as in Example 3. The water content of the sump product, i.e., pure methylal, was below 0.1% by weight.

The preferred process is described in FIG. 1.

The raw material 3 and the recycled stream 6 are separated in the under lower pressure operating column 1 into a distillate 4 consisting of methylal, a little methanol and in some cases methyl formate, and a sump product 5 consisting of methanol and in some cases water. The distillate of the column 1 (stream 4) is separated in the under higher pressure operating column 2 in a sump product consisting of pure methylal (stream 8); a side stream 6 consisting of methylal with an in relation to the stream 4, an increased concentration of methanol, and in some cases lower concentrations of methyl formate, which is recycled to the column 1, and in some cases a mainly methyl formate consisting distillate (stream 7).

Figure 2:
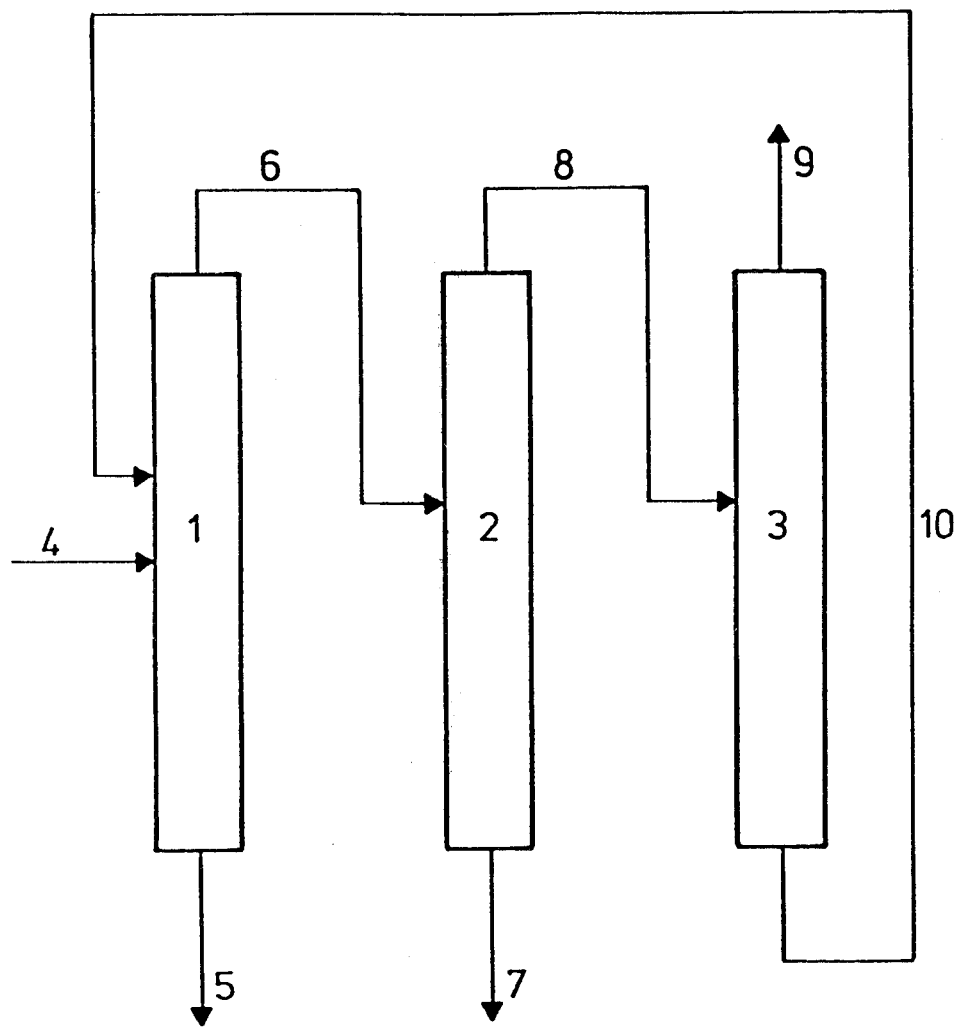
FIG. 2 is a schematic diagram of a second embodiment of an arrangement of columns for conducting the process according to the invention.

The process is also possible according to FIG. 2.

The raw material 4 and the recycled stream 10 are separated in the under lower pressure operating column 1 in a distillate 6 consisting of methylal, some methanol and lower boiling substances, e.g. methyl formate, and a sump product 5 consisting of methanol and in some cases water. The stream 6 is separated in the column 2, which is operated under a higher pressure than column 1, in a sump product 7 consisting of pure methylal and the distillate 8 consisting of methylal with a higher concentration of methanol in relation to stream 6. The stream 8 is separated in the column 3 in a distillate 9 with a high concentration of methyl formate and a sump product 10 consisting mainly of methylal with, in relation to the stream 6, an increased concentration of methanol, which is recycled to the column 1.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the recovery of pure methylal from a feed mixture containing methanol and methylal, said process comprising: rectifying the feed mixture in a first stage to obtain a methylal-rich and methanol-poor distillate, and a substantially methylal-free and methanol-rich sump product; feeding the methylal-rich distillate of the first rectification into a second rectification stage and rectifying the distillate under a higher pressure than the first rectification to obtain a compound stream consisting essentially of methanol and methylal, and a pure methylal sump product; and recycling the compound stream into the first rectification said feed mixture and said compound streams being the only streams fed to said first stage and said methylal-rich distillate being the only stream fed to said second rectification stage.

2. A process according to claim 1, further comprising conducting the first rectification under a pressure of 1–22 bar absolute, conducting the second rectification under a pressure of 9–30 bar absolute, and wherein the second rectification is conducted under a pressure which is at least 8 bar higher than the pressure of the first rectification.

3. A process according to claim 1 or 2, wherein the compound stream product, consisting essentially of methanol and methylal, is withdrawn from the higher pressure second rectification at the stage head.

4. A process according to claim 1 or 2, wherein the feed mixture of methanol and methylal further consists of more readily boiling compounds than methanol and methylal, and wherein the more readily boiling compounds present in the raw material are removed at the stage head of the second rectification.

5. A process according to claim 2, wherein said first rectification is conducted under about normal pressure and said second rectification is conducted under a pressure of 10 bar absolute at the second rectification stage.

6. A process according to claim 2, wherein the feed mixture of methanol and methylal also consists essentially of more readily boiling compounds than methanol and methylal, and wherein the compound stream product consisting essentially of methanol, methylal and the more readily boiling compounds is separated from pure methylal removed at the sump, and further separated in a further rectification to obtain a methanol- and methylal-containing stream depleted of low-boiling compounds which is recycled to the first rectifying stage, and a distillate depleted in methanol and methylal is removed from the process, and pure methylal is recovered in the sump of the further stage.

7. A process according to claim 2, wherein said first rectification is conducted under a pressure of 1–2 bar absolute, and the second rectification is conducted under a pressure of 10–15 bar absolute, and wherein the second rectification is conducted under a pressure which is 10–12 bar higher than the pressure of the first rectification.

8. A process according to claim 2, wherein the weight ratio of the recycle stream to the azeotropic mixture passed to the second column is about 0.15:1–0.6:1.

9. A process according to claim 8, wherein said weight ratio is about 0.2:1–0.4:1.

10. A process according to claim 9, wherein the reflux ratio of the first column is 1 to 2 and the reflux ratio of the second column is 0.8:1.

11. A process according to claim 2, wherein the distillate from the second column includes about 70–85% by weight methylal.

12. A process according to claim 1 wherein said first rectification is conducted in a manner wherein said methylal-rich and methanol-poor distillate obtained is an azeotrope of about 95% methylal.

13. A process for the recovery of pure methylal from a feed mixture containing methanol and methylal, said process comprising: rectifying the feed mixture in a first stage to obtain a methylal-rich and methanol-poor distillate, and a substantially methylal-free and methanol-rich sump product; feeding the methylal-rich distillate of the first rectification into a second rectification stage and rectifying the distillate under a higher pressure than the first rectification to obtain a compound stream comprising methanol and methylal, and a pure methylal sump product; recycling the compound stream into the frist rectification; said feed mixture and said compound streams being the only streams fed to said first stage and said methylal-rich distillate being the only stream fed to said second rectification stage.

14. A process according to claim 13, further comprising conducting the first rectification under a pressure of 1–22 bar absolute, conducting the second rectification under a pressure of 9–30 bar absolute, and wherein the second rectification is conducted under a pressure which is at least 8 bar higher than the pressure of the first rectification.

15. A process according to claim 14, wherein said first rectification is conducted under about normal pressure and said second rectification is conducted under a pressure of 10 bar absolute at the second rectification stage.

16. A process according to claim 14, wherein the feed mixture of methanol and methylal also comprises more readily boiling compounds than methanol and methylal, and wherein the compound stream product comprising methanol, methylal and the more readily boiling compounds is separated from pure methylal removed at the sump, and further separated in a further rectification to obtain a methanol- and methylal-containing stream depleted of low-boiling compounds which is recycled to the first rectifying stage, and a distillate depleted in methanol and methylal is removed from the process, and pure methylal is recovered in the sump of the further stage.

17. A process according to claim 14, wherein said first rectification is conducted under a pressure of 1–2 bar absolute, and the second rectification is conducted under a pressure of 10–15 bar absolute, and wherein the second rectification is conducted under a pressure which is 10–12 bar higher than the pressure of the first rectification.

18. A process according to claim 14, wherein the weight ratio of the recycle stream to the azeotropic mixture passed to the second column is about 0.15:1–0.6:1.

19. A process according to claim 18, wherein said weight ratio is about 0.2:1–0.4:1.

20. A process according to claim 19, wherein the reflux ratio of the first column is 1 to 2 and the reflux ratio of the second column is 0.8:1.

21. A process according to claim 19, wherein the distillate from the second column includes about 70–85% by weight methylal.

22. A process according to claim 13, wherein the compound stream product, comprising methanol and methylal, is withdrawn from the higher pressure second rectification at the stage head.

23. A process according to claim 13, wherein the feed mixture of methanol and methylal also comprises more readily boiling compounds than methanol and methylal, and wherein the more readily boiling compounds present in the raw material are removed at the stage head of the second rectification.

24. A process according to claim 13, wherein said first rectification is conducted in a manner wherein said methylal-rich and methanol-poor distillate obtained is an azeotrope comprising about 95% methylal.

* * * * *